Dec. 19, 1972 H. A. JOHNSON, JR Plant Pat. 3,274
STRAWBERRY PLANT
Filed April 8, 1971
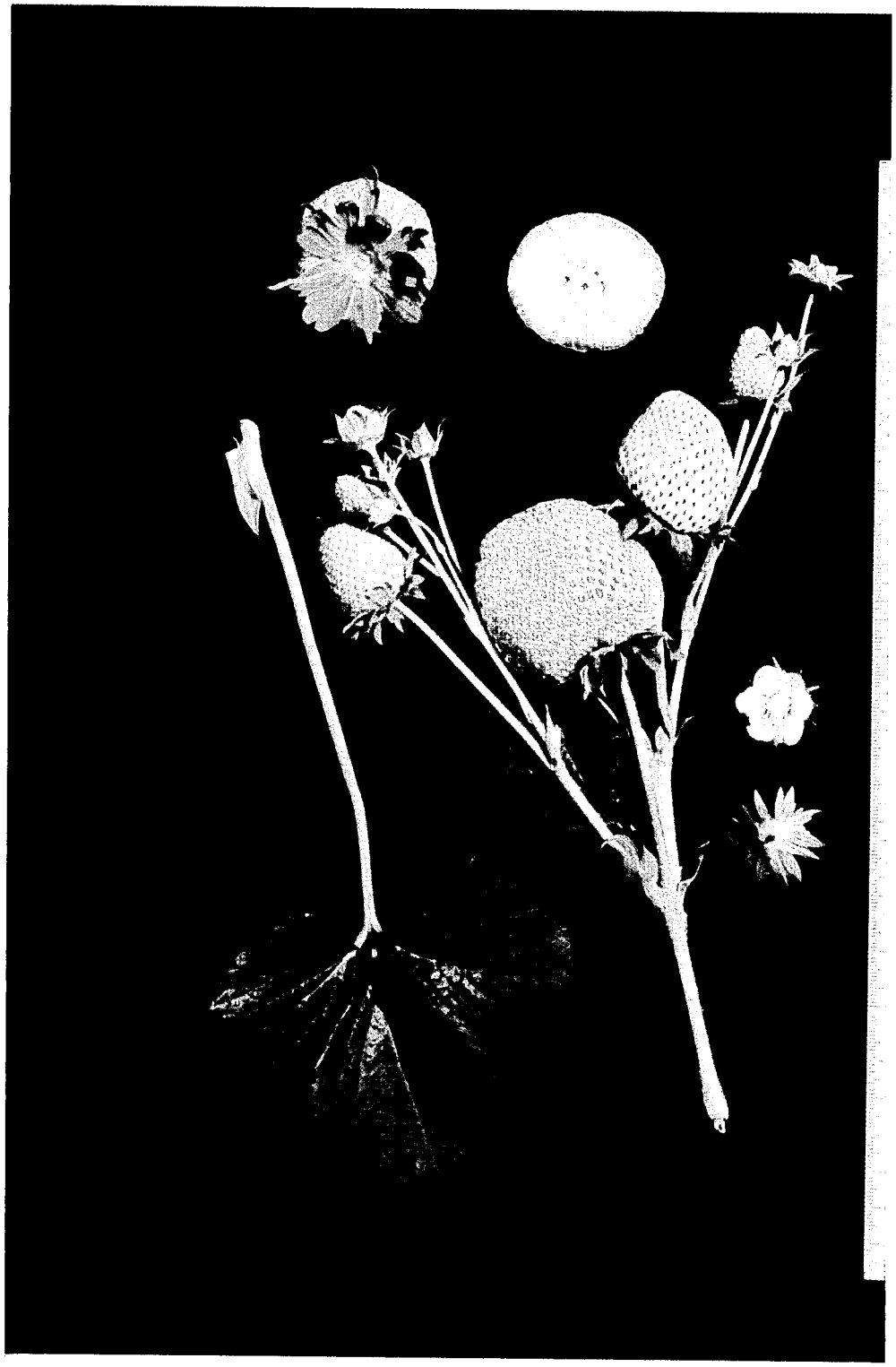
HAROLD A. JOHNSON, JR.
Townsend and Townsend United States Patent Office Plant Pat. 3,274

Patented Dec. 19, 1972

3,274

STRAWBERRY PLANT

Harold A. Johnson, Jr., Watsonville, Calif., assignor to Driscoll Strawberry Associates, Inc., Watsonville, Calif.

Filed Apr. 8, 1971, Ser. No. 132,621
Int. Cl. A01h 5/03
U.S. Cl. Plt.—49 1 Claim This invention relates to a new and distinct variety of strawberry plant which is the result of a cross of the unpatented variety known to The Strawberry Institute of California as Selection L44.1 and The Strawberry Institute of California Selection E2, Pat. No. 2,611.

The seedlings resulting from the aforementioned cross were grown and asexually multiplied in Shasta County, Calif., and tested in the fruiting beds on the propetry of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Plant parts of the new variety, typical in size, shape and color are pictured in the accompanying photograph. A berry in cross section illustrates flesh color and characteristic core cavity. The inflorescence pictured illustrates typical branching and relative size about the middle of June. The picture shows the presence of two secondary peduncles, the most prevalent number, but often there are three present on a single inflorescence. The picture also shows green tertiary and quaternary fruit that will eventually ripen. The leaf shown is typical in appearance and size, and the flower is also typical of primary and secondary flowers during this period of the year.

The novel plant is medium in size and vigor. This variety is typically everbearing with the ability for high production during the entire first year even when planted after receiving excessive chilling before being planted. The primary berries of the crown crop, the crop produced from buds that are initiated in the crown at the nursery, produces fruit that is relatively small in comparison to the E2 everbearing variety, Plant Pat. No. 2,611. However, the main crop, the crop produced subsequent to the crown crop, produces fruit that is large in size with many inflorescences produced on each plant. High production potential and high quality fruit are distinct characteristics of this new variety. The fertility of the achenes is generally excellent giving the fruit a surface free of ridges, ribs or malformation. The fruit is also distinct in that the flesh and epidermis is firm and the seed is exerted. These attributes give the fruit the ability to withstand the agitation usually inflicted on strawberries in transit to distant markets. If this variety is planted during January, the main crop comes into fruiting during the last of May. The production during the second fruiting year also usually commences during May and is large and distinct. The production continues until fall, both during the first and second year of production.

If the plant of this new variety is not affected by the Two-Spotted Mite, the plant is generally as large as the Goldsmith, Plant Pat. No. 1,735. The leaflet size is generally smaller, however, with the outline of the central leaflet generally round with sharp distinct serrations that are generally cupped downward. Individual leaflets may be darker in color than Goldsmith, but the total plant color seen at a distance may give a lighter appearance than Goldsmith, especially if the plants are infected with the Two-Spotted Mite. The petiole length is generally equal to that of Goldsmith and the occurrence of bracts on the petiole is rare and small if present.

Pedicels holding the primary berry generally originate from the axil formed by the union of two secondary peduncles. It is rare to find the pedicel branching from one of the secondary peduncles. The fruit shape is consistently medium to short wedge in outline with conic berries being the exception. The shoulders of the fruit at the calyx end are round and rarely necked. The variety has the distinction of producing large berries but if the vigor of the plant is weak the excessive fruit produced per plant results in smaller fruit size.

The dessert quality of this new variety is good and is sweeter to the taste than the Goldsmith variety. There is a generally strong but pleasant strawberry aroma peculiar to the flesh of this variety and is more noticeable than in the Goldsmith variety.

Individual flowers are large but not larger than Goldsmith. The diameter of the calyx of the new variety is larger and more serrated than that of Goldsmith. The prevalence of serrations on individual sepals is a distinct characteristic of this variety. Serrations are often present even on sepals coming from tertiary fruit.

This new variety appears to have less tolerance to the Two-Spotted Mite than the Goldsmith variety and has the same susceptibility to mildew as Goldsmith. It also seems to be quite susceptible to bronzing, the damage done by thrip during late spring and summer periods. It has not been completely tested against the Verticillium or the Red Stele diseases. As a seedling and selection, this variety withstood the natural invasion of certain virus components found in central California without losing its ability to produce.

The varietal characteristics of the novel plant, described below in detail, were observed mainly during the first fruiting season, but reference is also made to the appearance during the second fruiting year. Observations were made in the Watsonville area of California which is a cool coastal area near the Pacific Ocean. The color terminology is in accordance with Ridgeways Color Standards and Nomenclature (1912 Edition).

*Plants*

Medium in size and vigorous if given ample nutrients and chilling before being planted. It has an extensive root system.

*Leaves*

Medium in size. The central leaflet is usually 5 to 7 cm. in length with the width only slightly less than the length giving the central leaflet a round shape when viewing the outline. Petioles vary in length but are usually 12 to 15 cm. from their base to the petiolules if plants are growing vigorously. Petiolules are generally small and less than 8 mm. in length during the summer period. Bracts are rarely found on petioles and if present are small. Leaflet serrations are abundant and are deep and acute at the apex. The apex of serrations are often cupped downward. The color of the upper side of leaflet at Watsonville in August is Empire Green, Plate No. XXXII.

*Runners*

Runners are vigorous but only medium in abundance both at the nursey and in the fruiting beds.

*Inflorescence*

The inflorescence is mostly 20 to 25 cm. in length depending on the time of year. The common peduncle is generally 5 to 10 cm. Secondary peduncles vary from 2 to 3 in number with 2 being the predominant amount. Primary berries usually ripen first, with primary and secondary ripening at the same time being a rarity. Tertiary and quaternary fruit are abundant on any given inflorescence. Hair on the pedicels 20 mm. below tertiary flowers lays against and is parallel with the pedicel. The pedicels holding the primary berries usually originate at the axial formed by the union of peduncles, but may originate from one of the peduncles at a point near the axil. Flowers are large and may be visible above the plant during most of the summer period. The number of petals per flower averages between 5 to 7. Anthers produce an abundance of pollen during the total fruiting season.

*Fruit*

Crown crop berries are small to medium in size and may produce seeds that are exerted giving berries a seedy appearance. Subsequent crop fruit size is medium to large, but primaries are noticeably larger than secondaries. Primaries are mainly 40 to 45 mm. in length. The width is slightly less than the length. Fruit shape is mainly wedge in outline. Shoulders are rounded at the calyx end and not necked. The fruit surface is uniformly smooth with ribbing being unusual. Except for susceptibility to thrip, which gives the fruit a bronzed appearance, the fruit has a high gloss with a uniform spacing of the seeds. Seeds are generally medium to large and darken readily when exposed to direct sunlight. The berry has a medium high dessert quality. When berries are fully ripe they may become Carmine, Plate No. I. Fruit color under calyx generally remains white even after the fruit has ripened. Flesh color near the fruit surface is Scarlet, Plate No. I.

*Calyx*

Large in diameter with primaries during mid-summer averaging 40 to 50 mm. in diameter. The calyx of small fruit is large in relationship to fruit size. Sepals mostly overlap and are abundant. Sepals are elliptical ovate or obovate and serrations are abundant even on tertiary berries. Calyx is held free of the fruit surface, but rarely reflexed. Color of sepals on side facing the fruit is Varley's Green, Plate No. XVIII.

I claim:

1. The new and distinct variety of strawberry plant herein described and illustrated and identified by the characteristics enumerated above.

No references cited.

ROBERT E. BAGWILL, Primary Examiner